US005688522A

United States Patent [19]
Hardy

[11] Patent Number: 5,688,522
[45] Date of Patent: Nov. 18, 1997

[54] OINTMENT FOR WOUND TREATMENT

[75] Inventor: Craig J. Hardy, Skipton, United Kingdom

[73] Assignee: Johnson & Johnson Medical, Inc., Arlington, Tex.

[21] Appl. No.: 696,443

[22] Filed: Aug. 13, 1996

Related U.S. Application Data

[60] Continuation of Ser. No. 439,828, May 12, 1995, abandoned, which is a division of Ser. No. 204,730, Mar. 1, 1994, abandoned.

[30] Foreign Application Priority Data

Mar. 23, 1993 [GB] United Kingdom ............... 9306039

[51] Int. Cl.$^6$ ...................................................... A61L 15/00
[52] U.S. Cl. ................... 424/445; 514/777; 514/778; 514/779; 514/781; 514/944; 514/969
[58] Field of Search ..................... 514/777, 778, 514/779, 781, 944, 969; 424/445

[56] References Cited

U.S. PATENT DOCUMENTS

| | | |
|---|---|---|
| 4,503,034 | 3/1985 | Maupetit et al. ................ 424/80 |
| 4,643,856 | 2/1987 | Nichols . |
| 4,666,671 | 5/1987 | Purzycki et al. .................. 422/5 |
| 4,983,385 | 1/1991 | Hasegawa et al. ............... 424/78 |
| 5,084,427 | 1/1992 | Tsoucalas . |
| 5,338,541 | 8/1994 | Matz et al. . |
| 5,385,729 | 1/1995 | Prencipe et al. ............. 424/70.11 |
| 5,470,576 | 11/1995 | Patel .............................. 424/445 |

FOREIGN PATENT DOCUMENTS

| | | |
|---|---|---|
| 57-142913 | 9/1982 | Japan . |
| 2075837 | 11/1981 | United Kingdom . |
| 2 221 620 | 2/1990 | United Kingdom . |
| 8400111 | 1/1984 | WIPO . |

OTHER PUBLICATIONS

Kinnunen et al. in "Short Reports", pp. 148–150, 1991 (Acta Derm Venereo 2 (Stockh) 1991. 71:148–150).

*Primary Examiner*—Helen Lee
*Attorney, Agent, or Firm*—Andrew C. Farmer

[57] ABSTRACT

Wound healing compositions comprise from 1 to 20% by weight of a gel forming polysaccharide such as carboxymethyl cellulose and from 15 to 50% by weight of hexylene glycol. Such compositions are strongly antimicrobial, but show low toxicity to fibroblasts.

3 Claims, No Drawings

OINTMENT FOR WOUND TREATMENT

This is a continuation of application Ser. No. 08/439,828, filed May 12, 1995, now abandoned, which is a division of Ser. No. 08/204,730, filed Mar. 1, 1994, now abandoned.

This invention relates to an ointment for the treatment of wounds, and particularly for the treatment of ulcers.

Bactericidal ointments for the treatment of wounds are well known. Such ointments typically contain an antibiotic or an anti-bacterial agent in an inert vehicle or carrier, such as a paraffin base ointment or an oil-in-water emulsion. Antibiotics which are used include gentamycin sulphate and neomycin sulphate, while anti-bacterial agents include cetrimide, chlorhexidine gluconate and silver sulphadiazine.

Pharmaceutical ointments (and also cosmetic compositions) quite commonly contain a topically acceptable glycol, most usually propylene glycol. Such glycols have primarily been used in the past for their solvent and humectant properties. It is also known, however, that glycols possess some antibacterial and antifungal properties, and they have therefore also been used as preservatives in cosmetic preparations. Kinnunen and Koskela, Acta. Derm. Venereal (Stockholm) 71:148 to 150 (1991) report on the antimicrobial properties of aqueous solutions of three glycols (propylene glycol, hexylene glycol and 1,3-butylene glycol) against *Candida albicans, Staphylococcus aureus, Staphylococcus epidermidis, Streptococcus pyogenes, Streptococcus mitis* and *Escherichia coli* in vitro. The results indicated that hexylene glycol, in aqueous solution, is a more potent antimicrobial agent than propylene glycol and butylene glycol in vitro. According to the authors, these results speak in favour of using hexylene glycol in cosmetic and dermatological preparations instead of propylene glycol and 1,3-butylene glycol, but the authors also acknowledge that the antibacterial properties of dermatological formulations containing hexylene glycol might differ from those of aqueous solutions of hexylene glycol. Moreover, the results of these authors were contrary to the findings of Harb & Toama, Drug Cosm. Ind. 118:40–137 (1976), that butylene glycol should be more effective than other polyols against common bacteria and yeasts.

WO84/00111 discloses a heat sterilizable aqueous gel composition for use in the treatment of wounds, comprising a pharmaceutically acceptable glycol, preferably propylene glycol, and a cellulose derivative. According to the specification, the composition is believed to exert an inherent bacteriostatic action and to have a degree of activity against a range of viruses or mycelia. It is said to be effective as the sole agent in the treatment of clean superficial burns, cuts, wounds, abrasions and the like. However, it is also said that the compositions may include an antiseptic or an antibiotic.

EP-A-0047647 also discloses aqueous gel compositions for use in wound healing. The compositions according to this specification contain in solution each of the essential and semi-essential amino acids and maleic acid, the pH of the composition being in the range 6.5 to 8. Sodium carboxymethylcellulose is said to be particularly suitable as the gel-forming agent, but other cellulose derivatives such as microcrystalline cellulose are also said to be suitable, as are polysaccharides such as alginate, agarose and tragacanth, and also polyvinyl pyrrolidone. In the single example given in the specification, 1 kg of gel contains 13 g sodium carboxymethylcellulose, 10 g glycerol and 10 g propylene glycol in addition to the amino acids and maleic acid.

The gel compositions disclosed in EP-A-0047647 are said to be surprisingly resistant to bacterial and fungal infection in spite of the relatively high concentrations of nutrient material present. However, in view of the significant danger of infection of large wound areas, it is said to be often desirable to impose a wound-disinfection treatment between applications of the nutrient gel material.

GB-A-1397893 discloses a pharmaceutical composition for topical administration, comprising a steroid anti-inflammatory agent, water, at least one organic solvent, and a thickening agent. Representative thickening agents are hydroxyethylcellulose, hydroxypropylcellulose and carboxypolymethylene of molecular weight 940. According to the specification, the organic solvent may constitute from about 60% to 90% of the gel vehicle. Representative solvents are ethyl alcohol, isopropyl alcohol, propylene glycol, glycerine, 2-octyldodecanol and methyl pyrrolidine. A combination of isopropyl alcohol and propylene glycol in a 0.5:1 to 0.6:1 ratio by weight constituting from about 80% to 90% by weight of the gel vehicle is said to be particularly preferred.

GB-A-2091553 discloses a fast drying liquid vehicle for suspending pharmaceutical or cosmetic powders, comprising a monohydric alcoholic aqueous medium containing hydroxyethyl cellulose as the essential suspending agent, the alcohol content exceeding the water content but the water content being sufficient to prevent precipitation of the hydroxyethylcellulose. The alcohol is ethanol, methanol or isopropyl alcohol, and a polyhydric alcohol such as propylene glycol, glycerine and/or a polypropylene glycol may also be present. The use of a polyhydric alcohol is said to decrease the critical water level required in the hydroxyethylcellulose-containing alcoholic media.

GB-A-2075837 discloses a topical anti-inflammatory analgesic gel comprising ketoprofen and/or flurbiprofen as the effective ingredient, together with a pharmaceutically acceptable gel-forming excipient, a gel forming agent and, if required, a non-ionic surface-active agent and/or a solubilizing agent. According to the specification, the gel-forming excipient may include a glycol, and propylene glycol and butylene glycol are said to be preferred. Carboxyvinyl polymers, hydroxyethylcellulose, methylcellulose, carboxymethyl cellulose and alginic acid-propylene glycol ester are said to be suitable gel-forming agents.

CA-A-1049409 discloses a process for the production of a pharmaceutical composition suitable for topical application, incorporating a topically active steroid and a topically active antimicrobial agent. The process comprises the steps of:

a) dissolving the steroid in a solvent consisting essentially of a topically acceptable polyol and from 0 to 25% by weight, based on the weight of the composition, of a topically acceptable alcohol;

b) adding to the glycol solution of step a) from 0.5% to 5% by weight based on the weight of the final composition, of a cellulose ingredient selected from the group consisting of hydroxypropylcellulose and hydroxypropylmethylcellulose;

c) adding to the product of step b) an aqueous solution of neomycin salt and, where the neomycin salt is other than neomycin hydrochloride;

d) adding a pharmaceutically acceptable source of chloride ion, in an amount sufficient to produce a clear gel.

Glycerine, ethylene glycol, propylene glycol, butylene glycol and the like are said to be suitable polyols for use in the process.

EP-A-0393299 discloses a water-base gel which may be sterilized by means of γ radiation. The gel contains carboxypolymethylene, which is stabilized with the aid of polyvalent alcohols, such as ethylene glycol, glycerine, propylene glycol and hexylene glycol.

We have now found that hexylene glycol, when incorporated in a pharmaceutically acceptable gel vehicle, is highly effective against a range of infectious organisms, such as *Staphylococcus aureus, Bacillus subtilis, Escherichia coil* and *Aspergillus niger*. Indeed, hexylene glycol is so effective that gel compositions containing it compare very favourably with commercially available antiseptic ointments, even in the absence of added antibacterial agents. This is in marked contrast to the use of propylene glycol in prior art compositions merely as a bacteriostatic agent.

We have also found that hexylene glycol is surprisingly non-cytotoxic. Thus, although hexylene glycol is strikingly more effective than propylene glycol against bacteria, it is of very similar toxicity to propylene glycol against fibroblasts. This means that compositions containing hexylene glycol are markedly less inhibitory to the growth of cells involved in wound repair than are conventional wound treatment compositions of comparable effectiveness against bacteria.

According to the present invention, there is provided an aqueous wound treatment composition, comprising from 1 to 20% by weight of a gel-forming polysaccharide (which expression is intended to include polysaccharide derivatives), and from 15 to 50% by weight of hexylene glycol. Preferred compositions contain from 1 to 15% by weight of gel-forming polysaccharide, eg. from 1 to 10% by weight.

Preferably, the gel-forming polysaccharide is a cellulose derivative such as carboxymethyl cellulose or hydroxyethyl cellulose. A particularly preferred form of carboxymethyl cellulose is available under the Trade Mark Aquasorb. This has somewhat reduced solubility compared with other forms of carboxymethyl cellulose which are commercially available, and this has the advantage that compositions comprising Aquasorb are more readily removed from the bed of wound by washing. More soluble cellulose derivatives have a tendency to form a sticky film which is less readily removed from the wound bed.

The compositions according to the invention may comprise a mixture of two or more gel-forming agents. For example, the compositions may comprise a mixture of carboxymethyl cellulose and sodium alginate. Particularly preferred compositions comprise from 1 to 5% by weight of carboxymethyl cellulose, and from 1.5 to 6% by weight of sodium alginate.

In general, the gel-forming polysaccharide and the amount thereof are chosen so that the composition has a viscosity of from $10^5$ to $10^6$ cps, and preferably from $4\times10^5$ to $7\times10^5$ cps, as measured in accordance with ASTM D-2196-86 using a Brookfield Viscometer and a no. 6 spindle at a rotational speed of 1 rpm.

The compositions according to the invention may also contain minor amounts of other components. For example, the compositions may contain small amounts, e.g. up to 2% by weight, and more preferably up to about 1% by weight, of salts such as sodium chloride. The compositions may also contain vitamins and minerals known to be therapeutic, such as vitamin C and zinc. Furthermore, the compositions may contain collagen and wound-healing agents such as polypeptide growth factors (including TGFβ), chitin and its derivatives, hyaluronic acid and high mannuronate alginate. Preferably, however, the compositions according to the invention are free of antibacterial agents other than hexylene glycol.

Preferably, the hexylene glycol constitutes from 25 to 35% by weight of the composition according to the invention.

The compositions of the invention may be made by dispersing the gel-forming polysaccharide in the hexylene glycol, and then stirring the hexylene glycol dispersion slowly into water at an elevated temperature, such as from 40° C. to 80° C., e.g. 60° C. Stirring is then maintained until the formulation has thickened. Any other components, such as salts, may conveniently be dissolved in the water before addition of the hexylene glycol dispersion.

After mixing, the compositions may be sterilized by any suitable means, such as by autoclaving.

It has also been found that hexylene glycol-containing aqueous gels may be dried to form materials (and, in particular, films) which are useful in the treatment of wounds. In an alternative aspect, therefore, the present invention provides a wound treatment composition comprising from 15 to 80% by weight hexylene glycol, from 2 to 60% by weight of a gel-forming polysaccharide and from 0 to 40% by weight of water. Preferably, the composition is in the form of a film less than 10 mm in thickness, and more preferably from 0.1 to 2 mm thick.

The invention is further illustrated by reference to the following Examples.

EXAMPLE 1

Comparison of hexylene glycol, butylene glycol and propylene glycol gel formulations against *Staphylococcus aureus*.

Gels were prepared by mixing 2.0% Natrosol 250HX Pharm. (hydroxyethyl cellulose) 0.9% sodium chloride, the amounts of propylene, butylene or hexylene glycol specified in Table 1, and water. Each gel was tested according to the following protocol:

19.8 ml of the gel was placed in a sterile vial and held at 22° C.±1° C. for ten minutes to allow equilibration. 0.2 ml of a 1 to $3\times10^8$/ml suspension of *Staphylococcus aureus* NCTC 4163 was then added. At zero time, and at each pre-selected sample time, 1 ml of the gel mixture was removed and placed in 99 ml of Tween Peptone (TP) medium. After mixing well and further incubation for 5 minutes, the sample was serially diluted using 9 ml volumes of TP medium as the diluent. Each dilution was then filtered through a 0.22 μm pore size membrane filter, which was then washed with TP medium. The filters were then placed on Tryptone Soy Agar plates and incubated at 35° C.±1° C. for up to five days. Bacterial colonies were then counted.

The results are set out in Table 1. The figures in the Table show the number of organisms recovered (expressed as the $\log_{10}$) after exposure to the glycol-containing gels for the specified periods of time. It will be seen that exposure to hexylene-glycol at a concentration of 35% for as little as one minute was sufficient to leave no detectable survivors, but no substantial antibacterial effect was obtained with propylene glycol or butylene glycol at this concentration even after one hour's exposure. Also noteworthy is the fact that the number of organisms surviving after exposure to 15% hexylene glycol gel for an hour was approximately 13 times (ie. 1.5 $\log_{10}$ units) lower than the number surviving after exposure to 50% propylene glycol gel for the same length of time.

TABLE 1

| Glycol | % | Exposure time | | | | |
| --- | --- | --- | --- | --- | --- | --- |
| | | 1 min | 1 hr | 4 hr | 20 hr | 40 hr |
| Propylene | 15 | — | 6.9 | 5.8 | 5.1 | 4.1 |

TABLE 1-continued

| Glycol | % | Exposure time | | | | |
|---|---|---|---|---|---|---|
| | | 1 min | 1 hr | 4 hr | 20 hr | 40 hr |
| " | 25 | — | 6.1 | 5.4 | 5.6 | 4.7 |
| " | 35 | — | 5.9 | 5.5 | 4.9 | 2.6 |
| " | 50 | — | 5.0 | 5.1 | NDS | NDS |
| Butylene | 15 | — | 6.2 | 5.5 | 4.4 | 4.6 |
| " | 25 | — | 6.1 | 5.8 | 3.6 | 2.3 |
| " | 35 | — | 6.1 | 5.6 | 2.3 | 1.3 |
| " | 50 | — | 6.0 | 4.9 | 1.3 | NDS |
| Hexylene | 15 | 4.1 | 3.5 | 3.4 | NDS | — |
| " | 25 | 2.5 | NDS | NDS | NDS | — |
| " | 35 | NDS | NDS | NDS | NDS | — |
| " | 50 | NDS | NDS | NDS | NDS | — |

— = not determined
NDS = no detectable survivors

EXAMPLE 2

Comparison of hexylene glycol gel composition with commercially available antibacterial compositions.

In this Example, a hexylene glycol-containing gel composition according to the invention was compared with two proprietary products against a range of bacteria and fungi. This proprietary products were Flamazine (a propylene glycol-containing gel composition containing silver sulphadiazine), and Scherisorb (a propylene glycol-containing gel composition containing no additional antibacterial). The hexylene glycol-containing gels were prepared as described in Example 1, except that a combination of 1.5% Aquasorb A250 (carboxymethylcellulose) and 1.5% Natrosol 250HX Pharm. was used in place of the 2% Natrosol. The experimental protocol was essentially as described in Example 1.

The results were as set out in Tables 2A–2C. It will be seen that the hexylene glycol-containing gels according to the invention demonstrated an antimicrobial effect which was markedly superior to that of Scherisorb, and comparable to that of Flamazine.

TABLE 2A

*B. subtilis*

| Test material | Exposure time | | |
|---|---|---|---|
| | 1 hour | 4 hours | 20 hours |
| Scherisorb | 6.1 | 6.0 | 5.2 |
| Flamazine | NDS | NDS | NDS |
| Hexylene glycol 25% | NDS | NDS | NDS |
| Hexylene glycol 35% | NDS | NDS | NDS |

TABLE 2B

*E. coli*

| Test material | Exposure time | | |
|---|---|---|---|
| | 1 hour | 4 hours | 20 hours |
| Scherisorb | 6.8 | 6.3 | c. 6 |
| Flamazine | 6.2 | 5.2 | NDS |
| Hexylene glycol 25% | 6.3 | 4.1 | NDS |
| Hexylene glycol 35% | 6.2 | 3.7 | NDS |

TABLE 2C

*A. niger*

| Test material | Exposure time | | |
|---|---|---|---|
| | 1 hour | 4 hours | 20 hours |
| Scherisorb | 6.6 | 6.3 | 3.8 |
| Flamazine | 5.8 | 5.5 | 2.1 |
| Hexylene glycol 25% | 5.4 | 4.8 | 2.8 |
| Hexylene glycol 35% | 6.0 | 5.2 | 2.2 |

EXAMPLE 3

Toxicity of hexylene glycol to fibroblasts.

The tests described in this Example are based on the test method described in BS5736:Part 10:1988-Method of test for toxicity to cells in culture of extracts from medical devices.

Hexylene glycol gels were prepared as described in Example 1. A stock or master solution of each gel was then made by mixing one gram of gel with 4 ml of growth medium. A series of doubling dilutions was subsequently prepared from the stock solutions and used in the tests. Propylene glycol gels were prepared from a mixture of 25% propylene glycol, 1.5% Aquasorb A250, 3.0% Protanal LF10/60 (sodium alginate) and water.

1 ml aliquots of each test solution were pipetted into wells of test plates containing confluent monolayers of L929 fibroblast cells. The plates were then reincubated in a humid atmosphere containing 5% carbon dioxide for a further 24 hours at 37° C., when the monolayers were examined for evidence of cell death. The results were set out in Table 3.

TABLE 3

| Sample | Dilution | | | | | |
|---|---|---|---|---|---|---|
| | 1:5 | 1:10 | 1:20 | 1:40 | 1:80 | 1:160 |
| Hexylene glycol (35%) | +(4) | +(4) | +(1) | –(0) | –(0) | –(0) |
| Hexylene glycol (25%) | +(4) | +(4) | –(0) | –(0) | –(0) | –(0) |
| Propylene glycol (25%) | +(2) | –(0) | –(0) | –(0) | –(0) | –(0) |

In the above Table, the degree of cytotoxicity is expressed in accordance with the following convention:

0—Monolayer complete, no cell death
1—Cell death, but not greater than 25% of the total
2—Cell death greater than 25%, but not greater than 50%
3—Cell death greater than 50%, but not greater than 75%
4—Cell death greater than 75%, monolayer may be completely destroyed.

The results demonstrate that there is relatively little difference between hexylene glycol gels and propylene glycol gels in their toxicity to fibroblasts. In particular, it may be noted that the 25% propylene glycol gel at 1:5 dilution was more toxic than the 35% hexylene glycol gel at 1:20 dilution, indicating a less than three-fold difference in toxicity on a weight basis. This may be contrasted with the situation described in Example 1, in which a 15% hexylene glycol gel was shown to be at least an order of magnitude more effective than a 50% propylene glycol gel against *Staph. aureus*.

It may also be noted that comparative tests with the commercially available Flamazine cream showed it to be extremely toxic to fibroblasts (greater than 75% cell death) at dilutions up to 1:1280.

I claim:

1. A method of forming a wound treatment composition comprising the steps of:

provided an aqueous wound treatment composition by mixing from 1 to 20% by weight of a gel-forming polysaccharide selected from the group consisting of carboxymethyl cellulose and hydroxyethyl cellulose, from 15 to 50% by weight of hexylene glycol, and water, the weight being based on the weight of the aqueous wound treatment composition; and drying the wound treatment composition.

2. The method of claim 1, wherein the aqueous wound treatment composition further comprises up to 1% by weight of sodium chloride based on the weight of the aqueous wound treatment composition.

3. The method of claim 1, wherein the aqueous wound treatment composition comprises from 25 to 35% by weight of hexylene glycol, based on the weight of the aqueous wound treatment composition.

* * * * *